United States Patent [19]

Dorgan et al.

[11] Patent Number: 5,066,670

[45] Date of Patent: Nov. 19, 1991

[54] MACROLIDE DERIVATIVES WITH PARASITICIDAL ACTIVITY

[75] Inventors: Roderick J. Dorgan, Epsom; Graham S. Macaulay, Tadworth, both of England

[73] Assignee: Beecham Group p.l.c.

[21] Appl. No.: 491,564

[22] Filed: Mar. 9, 1990

[30] Foreign Application Priority Data

Mar. 11, 1989 [GB] United Kingdom ............... 8905605

[51] Int. Cl.$^5$ ................. A61K 31/365; C07D 313/00; C07D 307/93
[52] U.S. Cl. .................................... 514/450; 549/264
[58] Field of Search .......................... 549/264; 514/450

[56] References Cited

U.S. PATENT DOCUMENTS 4,900,753  2/1990  Sutherland et al. ................ 549/264

FOREIGN PATENT DOCUMENTS 0254583  1/1988  European Pat. Off. .
0280928  9/1988  European Pat. Off. .
0284255  9/1988  European Pat. Off. .
0288205  10/1988  European Pat. Off. .

*Primary Examiner*—Johann Richter
*Attorney, Agent, or Firm*—Hopgood, Calimafde, Kalil, Blaustein & Judlowe

[57] ABSTRACT

Compounds of formula (I):

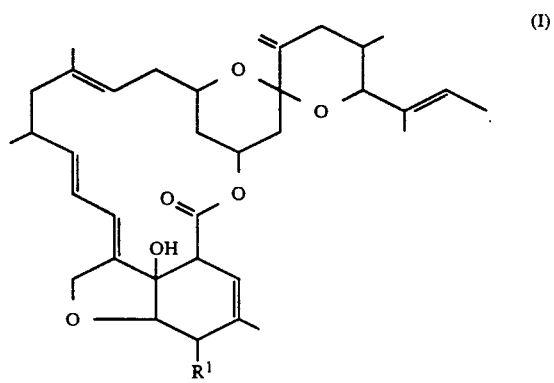

wherein $R^1$ is methoxy or optionally protected hydroxy have anthelmintic activity and are useful in the treatment of helminthiasis in humans and animals.

5 Claims, No Drawings

MACROLIDE DERIVATIVES WITH PARASITICIDAL ACTIVITY

The present invention relates to novel anthelmintically active materials, to processes for their production, to pharmaceutical formulations containing them, and to their use in human or veterinary medicine.

The present invention provides compounds of formula (I):

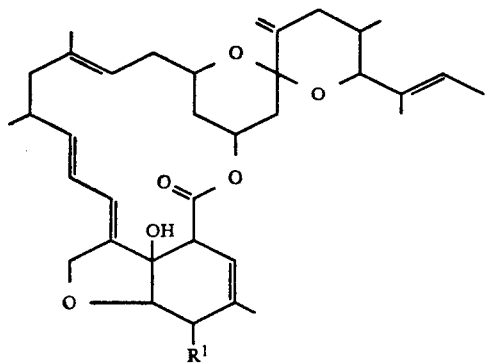

wherein $R^1$ is methoxy or optionally protected hydroxy.

Suitable protecting groups for hydroxy include TBDMS (t-butyldimethylsilyl), sulphonyl and acyl. Further suitable protecting groups are described in, for example, "Protective Groups in Organic Synthesis" Theodora W. Greene, Wiley-Interscience 1981 Ch 2, 10–86.

A further aspect of the invention provides a process for the preparation of a compound of formula (I), which process comprises reacting a compound of formula (II):

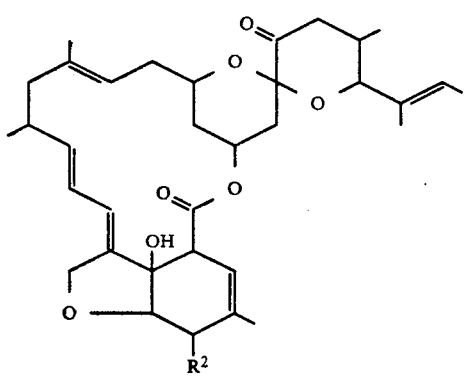

wherein $R^2$ is methoxy or protected hydroxy, with an organophosphorus compound, more particularly a Wittig reagent or equivalent thereof.

Suitable organophosphorus compounds are described in the "Lancaster Synthesis" catalogue 1986-7 Appendix 3 (Lancaster Synthesis Ltd., Eastgate, White Lund, Morecombe, Lancs. LA3 3DY).

The reaction is carried out under conventional conditions for this type of reaction. The Wittig reaction, and variations and modifications thereof, are described in "Organophosphorus reagents in Organic Synthesis" Ed. J.I.G. Cadogan, Academic Press 1979.

Appropriate Wittig reagents include phosphoranes of formula $(R)_3 P=CH_2$ (where R is $C_{1-6}$ alkyl or aryl, e.g. monocyclic aryl such as phenyl). Suitable reaction solvents include ethers such as tetrahydrofuran or diethyl ether or a dipolar aprotic solvent such as dimethylsulphoxide. The reaction may be carried out at any suitable temperature e.g. at 0° C.

Alternative processes for replacing an oxo group with a methylene group are described in EP-A-0 231 104, page 12, line 25 to page 13, line 14, and the application of these alternative processes to the compounds of formula (II) form a further aspect of this invention.

For example, a compound of formula (I) may be prepared by reacting a compound of formula (II) with an organometallic reagent generated from $CH_2(Hal)_2$—$Zn$—$TiCl_4$ (where Hal is an iodine or bromine atom). The reaction may be performed in a solvent such as tetrahydrofuran at, for example, room temperature.

The organometallic reagents for use in this reaction may be prepared according to the methods of Hibino et al Tet. Lett., 1985, 5579, Takai et al Tet. Lett. 1978, 2417 and Lombardo Tet. Lett., 1982, 4293.

In a further process, a compound of formula (I) may be prepared by reaction of the corresponding compound of formula (II) with an appropriate Grignard reagent $(CH_3)_3SiCH_2MgCl$ in a solvent such as diethyl ether at room temperature, followed by olefination in the presence of an acid e.g. sulphuric acid, in a solvent such as tetrahydrofuran at an elevated temperature e.g. at reflux.

The compound of formula (II) may be prepared by oxidizing a compound of formula (III):

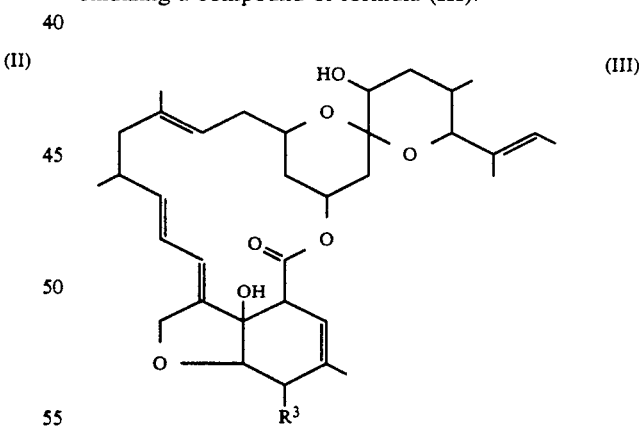

wherein $R^3$ is as defined above with respect to $R^2$.

Suitable oxidizing agents include DMSO/oxalyl chloride (Swern oxidation).

The compounds of formula (III) wherein $R^3$ is methoxy or hydroxy have been designated VM44864 and VM44866 respectively. These compounds, and their production by the fermentation of a Streptomyces microorganism, are described in EP-A-0 254 583 (U.S. Ser. No. 076,274). Their absolute configuration is believed to be as follows:

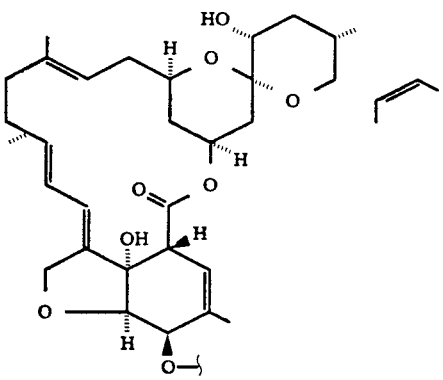

Each compound according to the invention is suitably provided in substantially pure form, for example at least 50% pure, suitably at least 60% pure, advantageously at least 75% pure, preferably at least 85% pure, more preferably at least 95% pure, especially at least 98% pure, all percentages being calculated as weight/weight. An impure or less pure form of the compound according to the invention may, for example, be used in the preparation of a more pure form of each same compound or of a related compound (for example a corresponding derivative) suitable for pharmaceuticial use.

The compounds of the invention have parasiticidal properties, for example against nematodes such as *Trichostrongylus colubriformis*, and are useful for the treatment of helminthiasis in animals such as mammals, including humans and domesticated animals (including farm animals).

Accordingly the present invention also provides a compound according to the invention, for use in the treatment of the human or animal body, especially for treating endo- and ectoparasitic infestations and particularly for treating helminthiasis of domestic and farm animals.

The term helminthiasis encompasses those diseases of man and animals caused by infestation with parasitic worms such as Strongyles, Ascarids, hookworms lungworms, filarial worms and whipworms. The compound may also be used against nematodes occurring in the soil or parasitic to plants.

The compounds of the invention are also active against Arthropods. The phylum Arthropoda comprises insects—such as biting flies, lice, bugs, beetles and fleas—and arachnids—such as mites and ticks.

The present invention thus provides a pesticidal composition comprising a compound according to the invention or a derivative thereof together with a suitable carrier or excipient, such as an aerosol formulation.

The present invention also provides a pharmaceutical or veterinary composition comprising a compound according to the invention or a pharmaceutically acceptable derivative thereof together with a pharmaceutically or veterinarily acceptable carrier or excipient.

The present invention also provides a method of treatment or prophylaxis of endo- and ectoparasitic infestations, especially helminthiasis, of animals, especially humans and domesticated mammals, which comprises administering an effective non-toxic amount of a compound according to the invention or a pharmaceutically acceptable derivative thereof, or a composition according to the invention, to a patient in need thereof.

The composition according to the invention may be formulated for administration in any convenient way for use in human or veterinary medicine, by analogy with other anthelmintics.

In suitable formulations the drug may be administered to animals orally (as a paste, drench, bolus, capsule or tablet), parenterally, percutaneously, as a food additive (e.g. granules, pellets or powder), or may be prepared as an aerosol spray formulation.

The compound of the invention may be formulated as a mixture with other anthelmintics, insecticides, acaricides or other pharmacologically active substances.

Suitably the composition consists of sufficient material to provide a dose of from 0.01 to 10 mg of active ingredient per kg of animal body weight per dose, more suitably 0.1 to 1 mg/kg per dose.

A composition according to the invention may suitably contain from 0.1% by weight, preferably from 10 to 60% by weight, of the compound according to the invention (based on the total weight of the composition), depending on the method of administration.

It will be appreciated that, in some cases, it will be advisable to repeat the dosing of the infected or potentially infected human or animal with the compound of the invention according to conventional dosage regimes used with anthelmintics.

The following Examples illustrate the invention.

EXAMPLE 1

22-Deoxy-22-methylene VM 44864

A stirred suspension of methyltriphenylphosphonium bromide (357 mg) in dry THF (10 ml) was treated with n-butyl lithium (0.625 ml; 1.6M in hexane) at 0° C. under nitrogen with stirring. The orange mixture was stirred at 0° C. for 20 minutes. A solution of 22-keto VM 44864 (100 mg), prepared as described in Example 8 of EP-A-0 288 205, in dry THF (5 ml) was added and the mixture stirred at room temperature for 2 h. Saturated ammonium chloride solution (50 ml) was added and the aqueous solution extracted with dichloromethane (3×30 ml). The combined extracts were dried, evaporated and purified by medium pressure Silica chromatography using Hexane:Ether (2:1) as eluent (75 mg) $m/z$ (E.I. 594 $M^+$).

$^{13}C$ nmr: 173.80, 146.45, 142.43, 139.63, 137.05, 135.83, 134.19, 123.40, 123.33, 120.68, 119.46, 118.36, 108.31, 98.16, 82.41, 80.24, 77.37, 76.83, 69.19, 68.25, 68.01, 57.70, 48.43, 45.57, 38.05, 37.09, 36.46, 34.84, 34.87, 34.66, 22.30, 19.84, 17.64, 15.48, 13.10, 10.88 ppm.

EXAMPLE 2

5-TBDMS-protected-22-deoxy-22-methylene VM 44866

To a stirred suspension of methyltriphenylphosphonium bromide (215 mg) in dry THF (10 ml) at 0° C. under nitrogen was added n-butyllithium (0.375 ml; 1.6M in hexane). The orange suspension was stirred at 0° C. for 25 mins then a solution of 5-TBDMS-22-keto VM 44866 (70 mg), prepared as described in Example 10 of EP-A-0288205, in dry THF (5 ml) was added. Th cooling bath was removed and the reaction stirred at room temperature for 1 hour. Saturated ammonium chloride solution (50 ml) was added and the aqueous solution extracted with dichloromethane. The organic extracts were washed with brine, dried and evaporated giving the crude title product which was used directly in the next step (Example 3).

EXAMPLE 3

22-deoxy-22-methylene VM 44866

To a solution of the crude product obtained in example 2 in methanol (10 ml) was added 4-toluene-sulphonic acid (10 mg) and the solution stirred at room temperature for 2 h. Water was added and the aqueous solution extracted with dichloromethane. The organic extracts were washed with brine, dried and evaporated. The product was purified by medium pressure chromatography on silica eluted with hexane/ether (2:1) to yield the title compound (40 mg) m/z (EI 580 m+).

$^{13}$C n.m.r.: 173.65, 146.51, 142.79, 139.43, 137.74, 137.04, 134.19, 123.39, 123.34, 120.76, 120.23, 118.04, 108.32, 98.18, 82.47, 80.12. 79.11. 69.16, 68.46, 68.01, 67.66, 48.41, 45.65, 38.07, 37.12. 36.54, 35.91, 34.90, 34.67, 22.27, 19.88, 17.67, 15.50, 13.13, 10.91 ppm.

We claim:

1. A compound of formula (I):

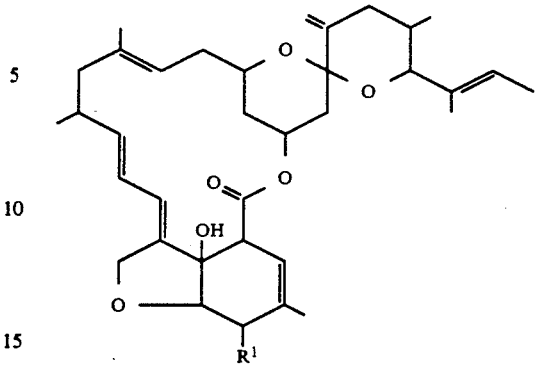

wherein $R^1$ is methoxy or optionally protected hydroxy.

2. A method of eradicating arthropod or nematode infestations, which method comprises applying an effective amount of a compound according to claim 1 to the arthropods or nematodes or to their environment.

3. A pesticidal composition comprising an effective amount of a compound according to claim 1 together with an inert carrier or excipient.

4. A pharmaceutical or veterinary composition comprising an anthelmintically effective amount of a compound according to claim 1 together with a pharmaceutically or veterinarily acceptable carrier or excipient.

5. A method of treatment or prophylaxis of endo-and ectoparasitic infestations of the human or animal body, which method comprises administering an effective amount of a compound according to claim 1, to a patient in need thereof.

* * * * *